US011571357B2

(12) United States Patent
Courtion et al.

(10) Patent No.: US 11,571,357 B2
(45) Date of Patent: Feb. 7, 2023

(54) VAGINAL HEALTH DIAGNOSTICS

(71) Applicant: Joylux, Inc., Seattle, WA (US)

(72) Inventors: Colette Donielle Courtion, Seattle, WA (US); Nicolas G. Loebel, Woodinville, WA (US); Ronald Oscar Zink, Mercer Island, WA (US)

(73) Assignee: Joylux, Inc., Seattle, WA (US)

( * ) Notice: Subject to any disclaimer, the term of this patent is extended or adjusted under 35 U.S.C. 154(b) by 305 days.

(21) Appl. No.: 16/776,318

(22) Filed: Jan. 29, 2020

(65) Prior Publication Data
US 2020/0237610 A1 Jul. 30, 2020

Related U.S. Application Data

(60) Provisional application No. 62/798,426, filed on Jan. 29, 2019.

(51) Int. Cl.
*A61H 19/00* (2006.01)
*A61N 5/06* (2006.01)
(Continued)

(52) U.S. Cl.
CPC ........... *A61H 19/44* (2013.01); *A61H 23/004* (2013.01); *A61H 23/0218* (2013.01); *A61N 5/0603* (2013.01); *A61N 5/0624* (2013.01); *A61N 5/0625* (2013.01); *A61H 2201/0207* (2013.01); *A61H 2201/10* (2013.01); *A61H 2201/501* (2013.01); *A61H 2201/5015* (2013.01); *A61H 2230/605* (2013.01); *A61H 2230/855* (2013.01);
(Continued)

(58) Field of Classification Search
CPC .... A61N 5/0603; A61N 5/0601; A61H 19/44; A61H 19/00; A61H 23/00; A61H 19/40; A61H 23/04; A61H 23/02; A61H 23/0254; A61H 23/2063; A63B 23/20; A61B 5/227
See application file for complete search history.

(56) References Cited

U.S. PATENT DOCUMENTS

D772,419 S    11/2016  Courtion et al.
D773,061 S    11/2016  Loebel et al.
(Continued)

OTHER PUBLICATIONS

Lanzafame et al., The rationale for photobiomodulation therapy of vaginal tissue for treatment of genitourinary syndrome of menopause: An analysis of its mechanisms of action, and current clinical outcomes, Photobiomodulation, Photomedicine, and Laser Surgery, vol. 37, No. 7, pp. 395-407, 2019.

*Primary Examiner* — Joseph D. Boecker
*Assistant Examiner* — Thomas W Greig
(74) *Attorney, Agent, or Firm* — Leanne Taveggia Farrell; Westman, Champlin & Koehler, P.A.

(57) ABSTRACT

A device including a semi-rigid shell forming an external surface with at least part of the shell adapted to contact tissue of a body cavity. The shell includes a treatment band formed around the shell, a first portion forming a rounded end of the device that is distal to the treatment band, and a second portion formed around the circumference of the shell and located proximal to the treatment band. The device further includes a vibration mechanism configured to case the shell to vibrate, a sensor configured to provide sensor data upon contact with the tissue, and a processor configured to receive the sensor data and to use the sensor data to produce parameters of the tissue.

20 Claims, 12 Drawing Sheets

(51) Int. Cl.
*A61H 23/00* (2006.01)
*A61H 23/02* (2006.01)

(52) U.S. Cl.
CPC ................ *A61N 2005/0611* (2013.01); *A61N 2005/0652* (2013.01)

(56) References Cited

U.S. PATENT DOCUMENTS

| | | | |
|---|---|---|---|
| 9,949,889 B2 | 4/2018 | Courtion et al. | |
| 10,166,168 B2 | 1/2019 | Courtion et al. | |
| 10,179,085 B2 | 1/2019 | Courtion et al. | |
| 10,537,491 B2 | 1/2020 | Courtion et al. | |
| 10,945,652 B1 * | 3/2021 | Wanderman | A61B 5/227 |
| 2003/0220589 A1 * | 11/2003 | Leivseth | A61B 5/227 |
| | | | 600/591 |
| 2006/0036188 A1 * | 2/2006 | Hoffman | A63B 23/20 |
| | | | 600/591 |
| 2014/0350333 A1 * | 11/2014 | Stout | A61H 19/44 |
| | | | 600/38 |
| 2015/0032032 A1 * | 1/2015 | Egorov | A61B 5/1077 |
| | | | 600/591 |
| 2015/0196802 A1 * | 7/2015 | Siegel | A63B 24/0062 |
| | | | 482/8 |
| 2015/0305971 A1 * | 10/2015 | Davis | A61H 19/44 |
| | | | 600/38 |
| 2016/0346610 A1 * | 12/2016 | Iglesias | A61B 5/4337 |
| 2017/0014624 A1 * | 1/2017 | Rohrer | A61N 1/36007 |
| 2017/0095398 A1 * | 4/2017 | Courtion | A61H 19/40 |
| 2017/0273860 A1 * | 9/2017 | Leivseth | A61B 5/227 |
| 2018/0185641 A1 * | 7/2018 | Peled | A61N 1/05 |
| 2019/0091097 A1 | 3/2019 | Courtion et al. | |
| 2020/0337941 A1 * | 10/2020 | Leivseth | A63B 23/20 |

* cited by examiner

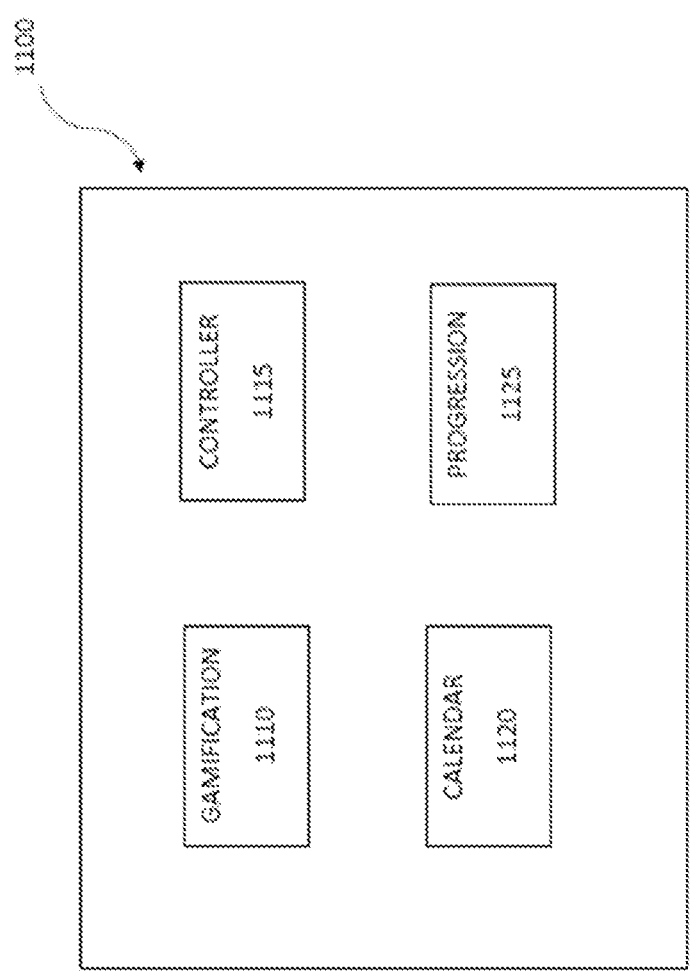

VAGINAL HEALTH DIAGNOSTICS

CROSS-REFERENCE OF RELATED APPLICATION

The present application is based on and claims the benefit of U.S. provisional patent application Ser. No. 62/798,426, filed Jan. 29, 2019, the content of which is hereby incorporated by reference in its entirety.

BACKGROUND

After childbirth or with aging, women can experience weakening or relaxing of their vaginal muscles. The relaxation of vaginal muscle or vaginal wall distension negatively impacts sexual intercourse, can cause intimacy and self-esteem problems, and can lead to urinary incontinence. Conventional solutions for tightening relaxed vaginal muscle include Kegel exercises and vaginal creams, but these are generally ineffective. Costly and invasive procedures for vaginal rejuvenation (e.g., vaginoplasty or laser vaginal rejuvenation) are another option, but these also fail to provide a safe, comfortable, affordable option for vaginal rejuvenation. Clinical treatment devices for insertion into the vagina to provide treatment are also available. However, the ability of these conventional devices appears to be limited. Furthermore, these devices are for treatment in a clinical setting, and are not designed to be a compact device for consumer or home use, nor are they designed to be enjoyable for the woman to use, making it less likely that regular treatments will occur and decreasing effectiveness of the devices.

The discussion above is merely provided for general background information and is not intended to be used as an aid in determining the scope of the claimed subject matter. The claimed subject matter is not limited to implementations that solve any or all disadvantages noted in the background.

SUMMARY

This invention relates generally to vaginally-insertable devices, more specifically to vaginal rejuvenation insertable devices.

In an embodiment, the vaginal rejuvenation insertable device includes a semi-rigid shell forming an external surface with at least part of the shell adapted to contact tissue of a body cavity. The shell includes a treatment band formed around the shell, a first portion forming a rounded end of the device that is distal to the treatment band, and a second portion formed around the circumference of the shell and located proximal to the treatment band. The device further includes a vibration mechanism configured to case the shell to vibrate, a sensor configured to provide sensor data upon contact of the tissue, and a processor configured to receive the sensor data and to use the sensor data to produce parameters of the tissue.

In another embodiment, a method is provided. The method includes activating a sensor that is within a treatment device while the treatment device is in contact with tissue of a body cavity, collecting sensor data representing a reaction of the tissue to the treatment device and using the sensor data to determine a parameter of the tissue.

In yet another embodiment, a device is configured to communicate with a treatment device. The device includes a user interface configured to receive subjective information from a user, a receiver configured to receive objective data from the treatment device, a processor implementing a decision matrix. The decision matrix is configured to use at least the subjective information and the objective data to select treatment settings for the treatment device. Further the device includes a transmitter configured to communicate the treatment setting to the treatment device.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIG. 11 is a block diagram of an app, in accordance with an embodiment.

DETAILED DESCRIPTION

The present description relates to a device configured to be used in a treatment plan for increasing vaginal strength and tone by collecting parameters of the tissue reaction to vibration and adjusting at least one of a light intensity, thermal energy, vibration pattern, vibration intensity and vibration duration according to the collected parameters.

After childbirth or with aging, women can experience the weakening or relaxing of their vaginal muscles. For example, childbirth and menopause can cause the proliferation of connective tissue, also known as vulvovaginal atrophy (VVA).

Vibration is known to stimulate the vulvar and vaginal tissues, which facilitates natural lubrication and helps maintain function. In addition to the effects that vibration has on medical conditions, i.e. fibroblasts, the vibration provides the benefit of massaging the vaginal tissue and providing a pleasure response in the user. This additional benefit means that the device may be used more frequently and for a longer period or duration of time, making it easier to have regular, more effective tissue treatments. The vibration not only has positive effects on the healing of tissue, but also provides the benefit of making the device enjoyable to use and potentially extending duration of use, allowing for usage of strengthening pelvic muscles, increasing pelvic muscle tone, renaturation and subsequent de novo formation.

In addition to vibration, light, particularly in the visible to far-infrared spectrum, may also be applied to the tissue. The light components may include lasers, light-emitting diodes (LEDs), supraluminous diodes (SLDs) and other noncoherent sources. Photobiomodulation therapy (PBMT) is used to stimulate synthesis of collagen and elastin in the treated tissue and supporting urethrovaginal sphincter and urethra, as well as promoting vasodilation in the vaginal and urethral submucosa.

Figure 1A:
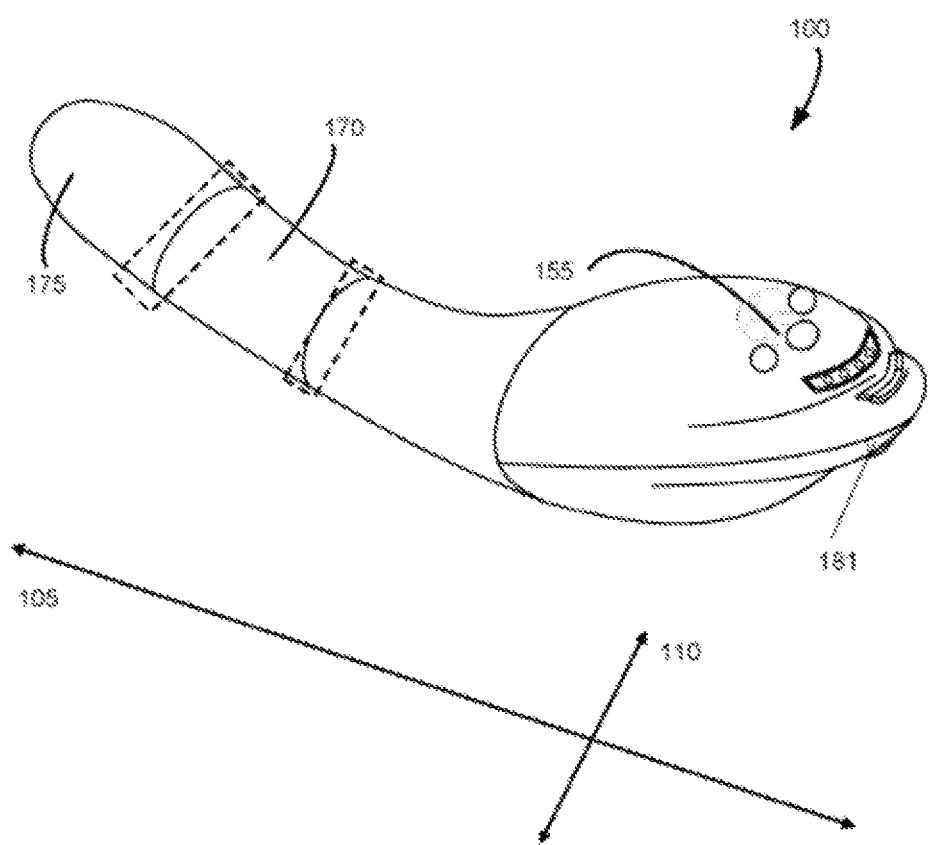
FIGS. 1A and 1B are examples of a device, in accordance with an embodiment.
Figure 1B:
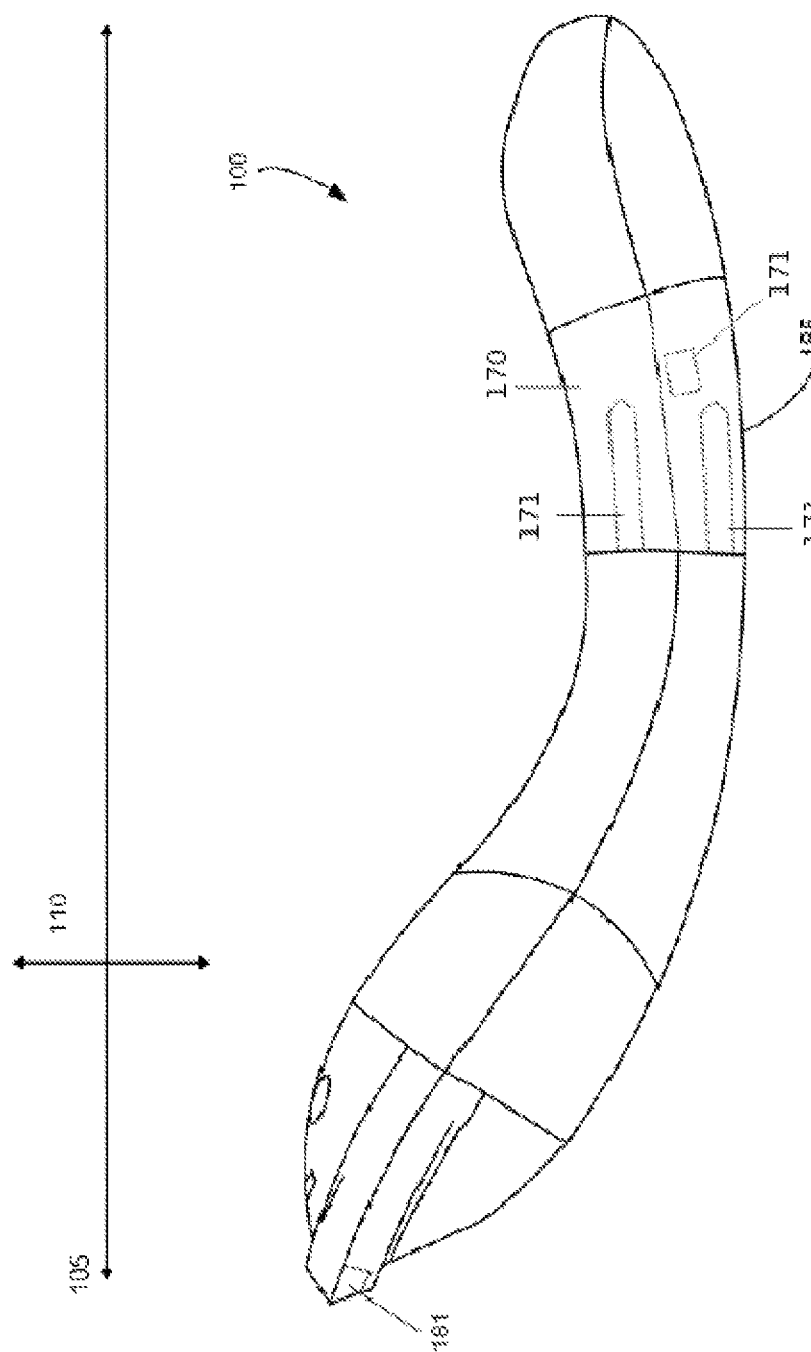

Further, thermal energy applied to the tissue has demonstrated that the controlled deposition and use of thermal energy on the vaginal wall are producing local effects in the vaginal mucosa and subsequent tissues in part or totally via a thermal heating mechanism FIGS. 1A-1B provide front perspective view and a side view, respectively, of an embodiment of a rejuvenation and therapeutic massage device 100, where the device 100 is a non-expanding, or semi-rigid, device in some embodiments. Device 100, includes a shell having a handle or end 155 designed to remain outside the orifice being treated, an opposite, insertable end 175 of the device designed to be inserted into the orifice being treated and an area, or treatment band 170, between ends 155 and 175 that is also designed to be inserted into the orifice being treated. Controls or buttons 156A-C are provided on end 155 and include power button 156A for turning device 100 on and off, a session length selection button 156B for selecting the temporal length of the treatment session, and a vibration mode button 156C for selecting a mode of vibration. An LED array 180 on end 155 provides visual feedback to indicate when the device has been turned on or off and the selected treatment session length. A connection port 181 on end 155 accepts a cable 150 that can be used to provide power to device 100 and to exchange data between device 100 and an external device. Sensors 171 and/or at least one light emitting component 140 is located within treatment band 170. In some embodiments, one or more of sensors 171 form part of shell 185 while in other embodiments, one or more of sensors 171 are located on top of shell 185 and in still other embodiments, one or more of sensors 171 are located within shell 185. Shell 185 encases a vibrating component 172, a power source 186 and a circuit board 188. In an alternative embodiment, the shell 185 in at least the treatment band 170 is transparent such that the light from the at least one light emitting component 140 may reach the tissue for treatment.

The light emitting component 140 may include light emitting diodes (LED), electric lamps, incandescent lamps, other electroluminescent lamps, or lasers. The emitted light is capable of applying a thermal load, or heat, to the vaginal mucosa surrounding the device 100. The light can be emitted in a range of 250-400 nm for disinfection or sterilization purposed and can kill bacteria and prevent infection, i.e. yeast infection, during use of the at least one light emitting component 140.

In an embodiment, the thermal load may also be produced by a temperature component 190 of the device 100. The temperature or range of temperatures is configured to produce heat to a depth that permits collagen melting and repair. The temperature component is configured to have a temperature limit to keep the temperature in a temperature range that can be specified by the user or by a protocol.

In the embodiment shown in FIGS. 1A-1B, the device is from 2-7 inches long along a vertical axis 105 with a diameter of from 1-3 inches along a horizontal axis 110. In other embodiments, the shape and size of the device 100 may vary. During use, a portion of the device, including at least insertable end 175 and treatment band 170, is placed in a body cavity, or cavity lumen such as the vaginal lumen.

Figure 2:
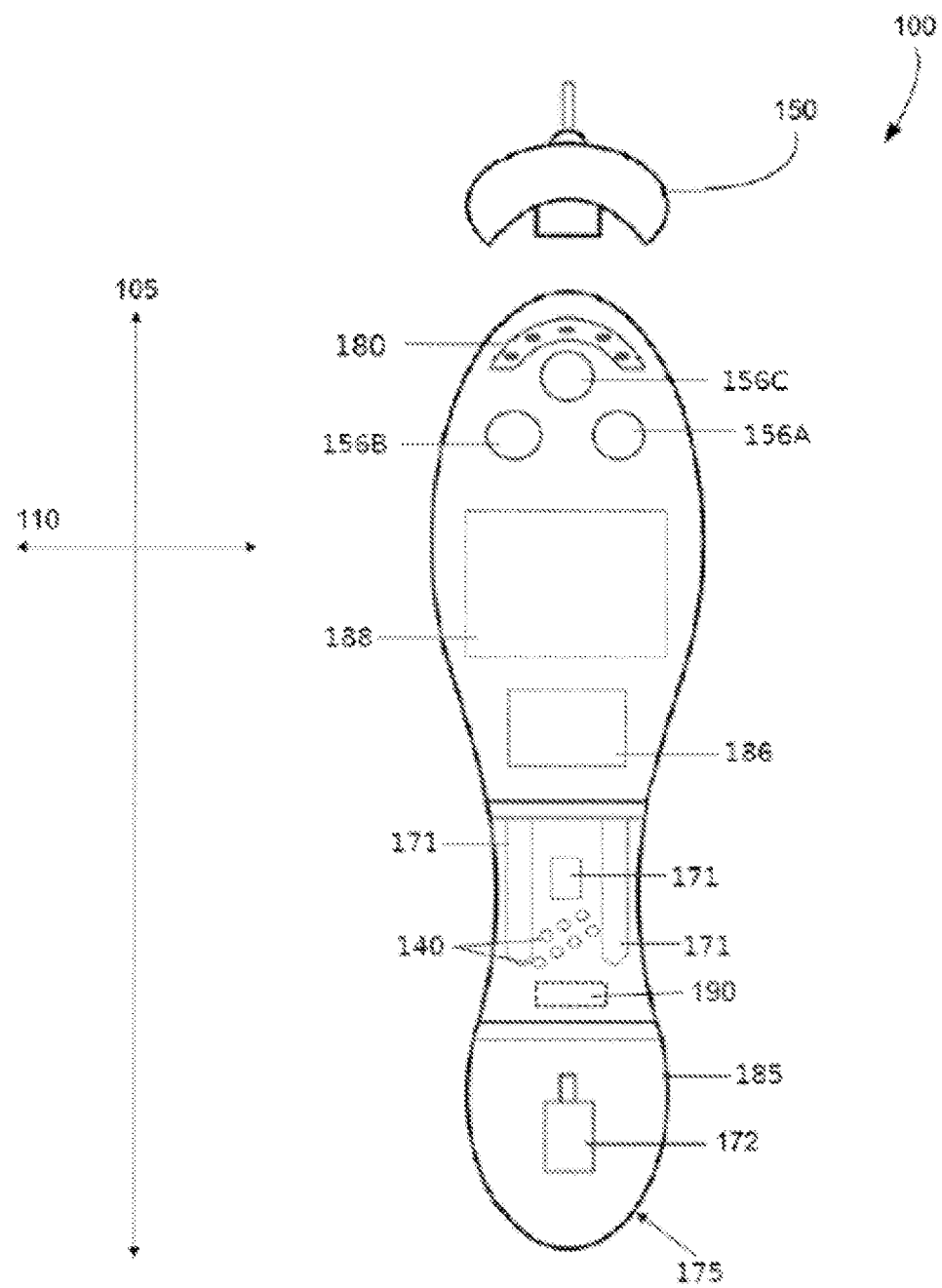
FIG. 2 is a diagrammatic view of the device of FIGS. 1A and 1B, in accordance with an embodiment.

In one embodiment, shell 185 of device 100 is made of a high-durometer medical-grade silicone material, is water-clear in color, and has a very slight deformability in structure. In another embodiment, the shell is made of an opaque liquid crystal polymer. In yet another embodiment, the shell of the device is made of both a high-dura meter medical-grade silicone material and a transparent liquid crystal polymer. In yet another embodiment, the shell 185 of the device 100 is made of both a high-durometer medical-grade silicone material. For example, as shown in a side view in FIG. 1B, the shell 185 of the device 100 can be transparent at a location where light-emitting diodes are located in the device (e.g., at treatment band 170) and opaque at locations where light-emitting diodes are not located, as illustrated in FIG. 2 which shows a diagrammatic front view of FIG. 1A-1B. Treatment band 170 of the device thus acts as a treatment window and is the area at which light is shone from the device 100 onto tissue inside the vagina to provide treatment to the tissue while the end 175 is inserted in the vagina.

In an embodiment, the device is waterproof (or water-resistant). Additionally, in an embodiment, the device 100 is resistant to a range of lubricant chemistries. The device is thus compatible with use of a customized medical-grade lubricant that matches the refractive index of the optical emitting surface to the tissue surfaces, such as through a water base, maximizing light transmission into the tissue and minimizing loss of light due to scattering.

The device illustrated in FIGS. 1A-1B and FIG. 2 is designed to be an at home use or as a Class 1 product and does not require trained individuals for use. It is also designed to be ergonomic for comfortable and convenient use. It is further portable, easily cleanable, can be battery-operated, and can be IPXn fluid ingress rated. It may be a handheld device, and some or all of the components can be integrated into or included on the device such that it can be a fully contained consumer handheld unit.

Vibrating device 172 includes one or more motors and one or more counterweights configured to operate in a range of frequencies such as 5-10 Hz, 8-10 Hz range, and 0-15 kHz (though it can also operate in other similar ranges, as desired). For example, one motor can operate in a frequency less than 10 Hz to provide vaginal rejuvenation and one or more other motors can operate in a frequency of up to 15 kHz to induce pleasure. As another example, a single motor provides both vaginal rejuvenation and induces pleasure. According to research, the 5-10 Hz range of vibration effects myofibril generation and collagen production, enhancing tissue regeneration, neocollagenesis, and rejuvenation of vaginal tissue. In some embodiments, vibrating device 172 vibrates in whatever range is determined to produce effective myofibril generation and collagen production. The one or more motors and one or more counterweights are flexibly coupled to the one or more portions of the inner wall of the shell 185 of the device 100. In one embodiment, the one or more motors and one or more counterweights are coupled to the one or more portions of the inner wall of the shell to maximize surface deflection or maximize offset of the shell to the one or more motors and one or more counterweights. In one embodiment, the one or more motors and one or more counterweights are coupled inline and paired, providing phases of vibration patterns along the vertical axis 105 of the device. The phases of vibration patterns can be selected by the user using vibration mode button 156C. In an alternative embodiment, the vibration patterns and frequency instructions may be selected and transmitted to the device 100 from an external device 500, as further described below in conjunction with FIG. 5.

In other embodiments, vibrating device 172 is constructed of a high-efficiency resonant drive mechanism, reducing power required to operate the device. The high-efficiency resonant drive mechanism includes a rare-earth magnetic stator surrounded by laminated armature pieces directing magnetic lines of flux to a spring-steel rotor. The armature includes anti-sense coils and the anti-sense coils periodically and continuously imbalance the magnetic force directed by the armature towards the rotor, causing the rotor to deflect in the direction of applied force. The resonant drive mechanism is configured for resonant operation at any desired frequency, with a preferred range of 5-10 Hz. The resonant drive mechanism can also be configured for resonant operation in an 8-10 Hz range, or at any frequency from 0-15 kHz. For example, one resonant drive mechanism can operate in a frequency less than 10 Hz to provide vaginal rejuvenation and one or more other resonant drive mechanism can operate in a frequency of up to 15 kHz to induce pleasure. A primary attribute of the high-efficiency resonant drive mechanism is that the high-efficiency resonant drive mechanism uses little drive energy for comparatively large mechanical deflections, has no moving or sliding parts which can wear, and includes simple construction not requiring expensive components. In one embodiment, the high-efficiency resonant drive mechanism's rotor is flexibly coupled to the outer walls of the device configured to maximize surface deflection or vibration of key, circumscribed portions of the device, rather than the entire device by default. The flexible coupling maximizes energy coupling to the vaginal mucosa rather than to the hand of a user of the device. Alternatively, in an alternative embodiment, repetitive pressure pulses may be applied to the tissue, for example, using a solid-state transducer, i.e. piezoelectric, a voice-coil transducer or a surface transducer.

In accordance with one embodiment, sensors 171 include force sensors that are arranged around the circumference of treatment band 170 of device 100. Examples of such force sensors include but are not limited to force-sensing resistors (FSR), strain gauges, pressure transducers, capacitive sensors, reverse piezoelectric transducers and accelerometers. In addition to a pressure or force type sensor, further sensors in the device may include sensors to detect the health of the user, for example, a sensor that indicates hydration levels to determine the amount of lubrication, pH levels, temperature, blood flow levels, electrical activity levels, tissue colorimetric effects, levels of various ions, other naturally, present chemistries and/or other diagnostic tools to determine vaginal health.

The power source 186, in one embodiment, is simply a connection to a low voltage power line from device 100 to a plug-in wall transformer. In other embodiments, power source 186 includes a radio frequency or other charging apparatus built into the device and one or more batteries. For example, in some embodiments power source 186 couples to a charging apparatus or charger through cable such as a universal serial bus (USB) connection such as a Micro-B plug, UC-E6 proprietary (non-USB) plug, Mini-B plug, Standard-A receptacle, Standard-A plug, Standard-B plug, micro USB or any other suitable connector including one or more pins necessary to charge the device. The charging apparatus can be configured to couple to a wall alternating current (AC) plug. In other embodiments, power source 186 is wirelessly or inductively charged via a base that includes a transmitting coil that magnetically couples with a receiving coil in the device to induce current in the receiving coil and charge the device. In still further embodiments, power source 186 is replaceable batteries.

Figure 3:
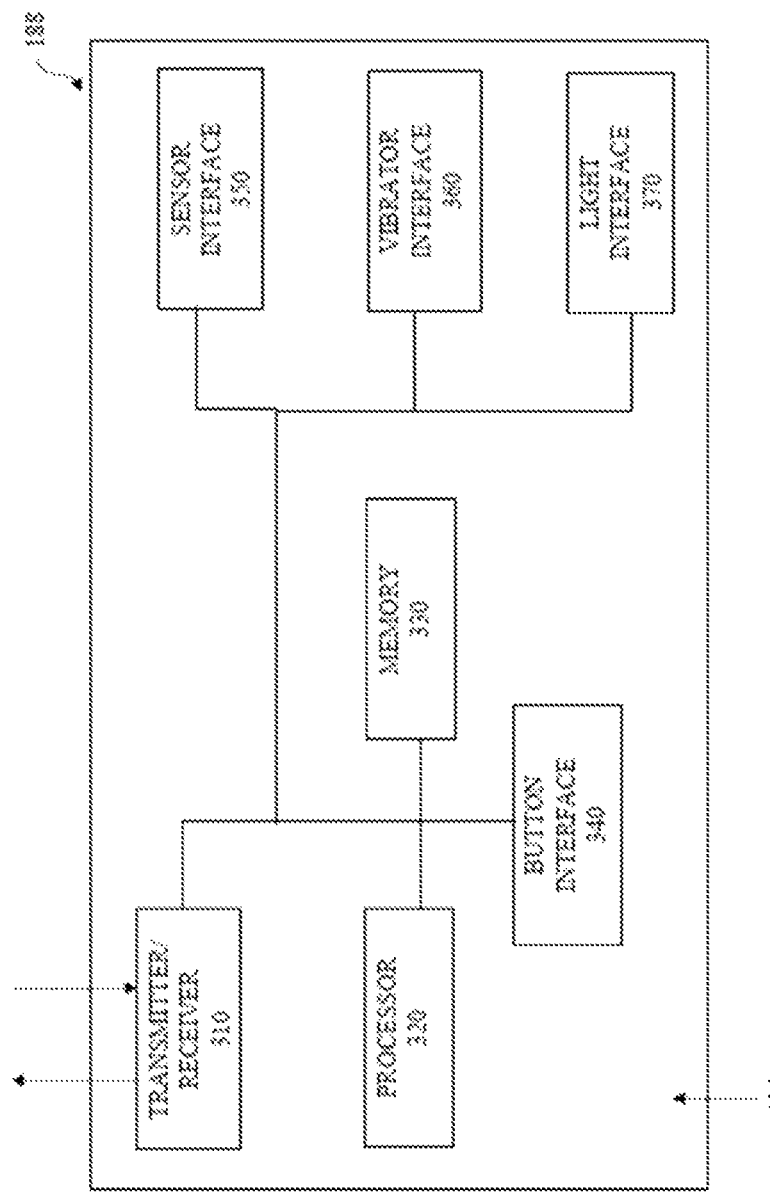
FIG. 3 is a block diagram of a circuit board of the device illustrated in FIGS. 1A-1B and FIG. 2, in accordance with an embodiment.

FIG. 3 provides a block diagram of the elements of circuit board 188 powered by power source 186. The circuit board includes a transmitter/receiver 310, a processor 320, a memory 330 a sensor interface 350, a vibrator interface 360 and a light interface 370.

In accordance with one embodiment, the transmitter/receiver 310 is configured to receive a communication from the external device 500 and transmit data from the processor 320, the memory 330 and/or the sensor interface 350, to the external device 500. In an embodiment, the transmitter/receiver 310 comprises a wireless component, such as a Bluetooth component, to enable a wireless data transfer. In an alternative embodiment, the receiver/transmitter 310 includes a wired connection, such as a USB type connector, to connect to the external device 500 for a wired data transfer. The wired connection may be connected at connection port 181 on end 155 of device 100.

The processor 320 executes instructions stored in memory 330 to process data signals received by the transmitter/receiver 310, sensor data received through sensor interface 350, button control signals received through button interface 340 and to issue control commands to vibrating device 172 through vibrator interface 360 and to light emitting components 140 through light interface 170 and may include various computing architectures including a complex instruction set computer (CISC) architecture, a reduced instruction set computer (RISC) architecture, or an architecture implementing a combination of instruction sets. Although only one device processor is shown, multiple processors may be included. The processors can include an arithmetic logic unit, a microprocessor, a general-purpose computer, or some other information appliance equipped to transmit, receive and process electronic data signals from the device memory 330 and other devices both shown and not shown in the figures.

The button interface 340 is configured to communicate with buttons 156A-C. When a button 156A-C on the device 100 is pressed, a signal is sent to the button interface 340 which in turns sends the signal to processor 320. Based on the signal received through button interface 340 and instructions stored in memory 330, processor 320 then generates command signals to one or more of vibrator interface 360 and/or light interface 370. In an embodiment, each button 156A-C has its own button interface 340 or in an alternative embodiment, the buttons 156A-C share a button interface.

The sensor interface 350 of the circuit board 188 is configured to receive sensor data from sensors 171 and to provide that sensor data to processor 320. Further, as discussed in conjunction with the discussion according to FIG. 4, the data received through the sensor interface 350 is either used by processor 320 to determine parameters of tissue around device 100 or is transferred to an external device through transmitter/receiver 310. Although only one sensor interface 350 is shown in FIG. 3, in an embodiment, each sensor has a sensor interface 350, thus the circuit board 188 has a plurality of sensor interfaces.

Similarly, the vibrator interface 360 communicates with the vibrating device 172 and the light interface 370 communicates with the at least one light emitting component 140 using a signal received from processor 320.

In addition to the device examples provided above, a variety of other designs can be used. Some embodiments include a rejuvenation and massage device capable of stimulating neocollagenesis and neoelastogenesis factors, while simultaneously engaging the female sexual response in order to maximize likelihood of repeated use of the product and thence assure clinical benefit. Some embodiments include a rejuvenation and massage device to effect toning and strengthening of the vaginal muscle tissue and enhance subsequent myofibril generation and neocollagenesis.

Figure 4:
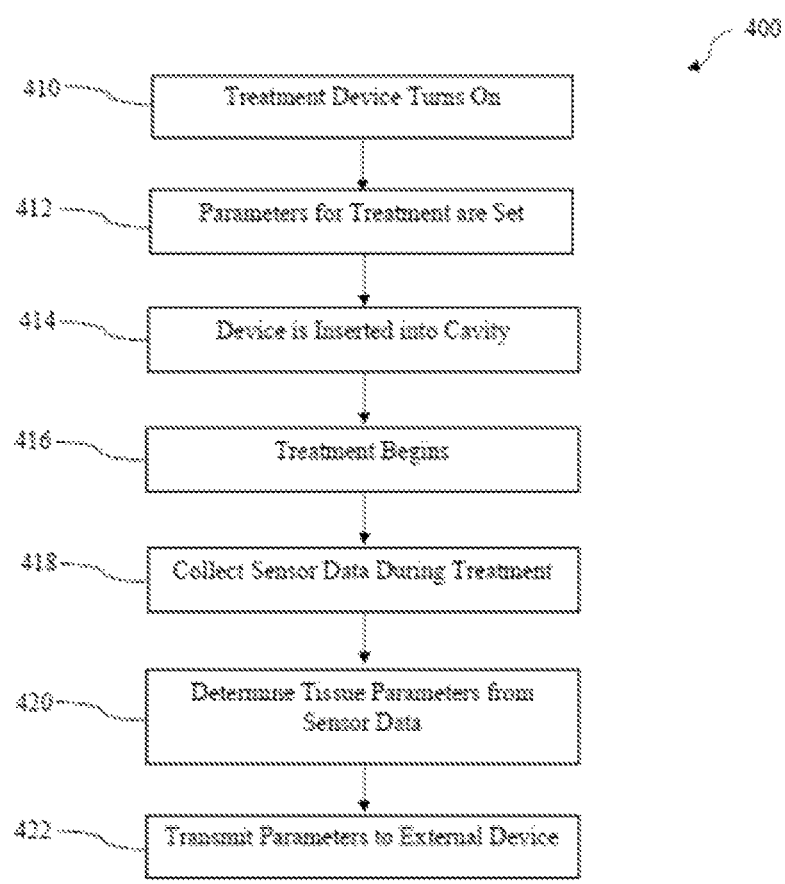
FIG. 4 is a flowchart of a method for a cavity treatment, in accordance with an embodiment.

FIG. 4 is a flowchart of one embodiment of a method 400 for cavity treatment. A device, such as device 100 of FIGS. 1A, 1B, 2 and 3 is turned on at step 410 and parameters for the treatment session are set in device 100 at step 412 using controls such as session length selection button 156B and vibration mode button 156C, automatically by processor 320 or via an external device as discussed further below. The user inserts the device into the cavity at step 414 such that the device contacts at least one surface of the cavity. At step 416, the treatment begins. During the treatment, sensor data is collected at step 418 and is used to determine one or more parameters of the cavity tissue and/or surrounding muscle at step 420. In accordance with one embodiment, the parameters of the cavity tissue and/or surrounding muscle are determined by internal processor 320 of device 100 while in other embodiments, the sensor data is transmitted to an external device that processes the data to determine the parameters of the cavity tissue and/or surrounding muscles. If the parameters of the cavity tissue and/or surrounding muscle are determined by internal processor 320, the parameters are stored in memory 330 and are optionally automatically transmitted to an external device using transmitter/receiver 310 at step 422.

In step 418, sensors 171 sense aspects of the cavity muscles and tissue as the muscle and tissue react to the treatment provided by the device such as the vibration of device 100. In accordance with one embodiment, force sensors are used as sensors 171 to measure the reaction forces of the tissue against device 100 during the vibration of device 100. The measured forces are then converted into characteristic parameters of the tissue at step 420. The parameters include, but are not limited to, the viscous, elastic and plastic deformation characteristics and combinations thereof, of the tissues that define the cavity wall. The viscosity, or viscous response of the tissue, is a measurement of the loss modulus of the tissue and indicates the ability of the tissue to dampen/absorb forces applied to the tissue. The elastic component, or spring response of the tissue, measures the elasticity of the tissue and indicates the rate at which the tissue returns to its previous shape when a force that deformed the tissue is reduced. A high spring component indicates a high elastic component of the tissue. The plastic component, or the plastic response of the tissue, measures the resting resistance or tension of the tissue in a distended position and indicates the degree to which the tissue is able to return to its previous shape given an unlimited amount of recovery time.

To determine the plasticity of the tissue, the force exerted by the tissue against the device is measured while an extremely low-frequency vibration or no vibration is applied. The elasticity and viscosity of the tissue is determined by measuring the force while vibrating device 172 generates a vibration. In particular, the vibration signal is used to decompose the measured force signal into an in-phase component and an out-of-phase component. The in-phase component represents the force due to the elasticity of the tissue while the out-of-phase component represents the delayed tissue recoil components due to the viscosity of the tissue. In accordance with one embodiment, an accelerometer is included in sensors 171 to measure the vibration signal. In other embodiments, a signal used to drive vibrating device 172 is used as the vibration signal.

The measurements of the viscosity, elasticity and plasticity of the tissue can be performed either while the user is trying to contract the muscles of the cavity or while the user is not trying to contract the muscles of the cavity. When the measurements are performed while the user is not trying to contract the muscles, the measured viscosity, elasticity and plasticity provide measures of the muscle tone of the tissue, or involuntary muscle reaction. When the measurements are performed while the user is trying to contract the muscles, the measured viscosity, elasticity and plasticity provide measures of the muscle strength of the tissue, or the voluntary muscle use. A user may have a muscle tone of the tissue in a medically satisfactory range, but a weaker muscle strength that may cause issues such as urinary incontinence. The reverse may also occur. A user may have a strong muscle strength in a medically satisfactory range, but a weak muscle tone according to a medical scale.

In one embodiment, the viscoelastoplastic responses of the tissue is measured by using a scanned technique. The frequency of the vibration is scanned from near zero to a predetermined high frequency level while holding the amplitude of the vibration constant. Alternatively, or additionally, the amplitude of the vibration can be scanned from near-zero to a predetermined high level while holding the frequency constant. The simultaneous scanning may be done either rad hoc or in response to inputs from the measurement devices (sensors 171). The resulting responses are detected either in the amplitude domain, e.g. measurement of the reaction distances, or in the time domain, e.g. measurement of the phase between the resultant reaction and the applied force. The overall frequency response of the system is measured to include resonant peaks, overtones, harmonics and subharmonics which make up the overall frequency response and provides the objective input data to derive the rheological, or viscoelastoplastic, parameters of the tissue.

Figure 10:
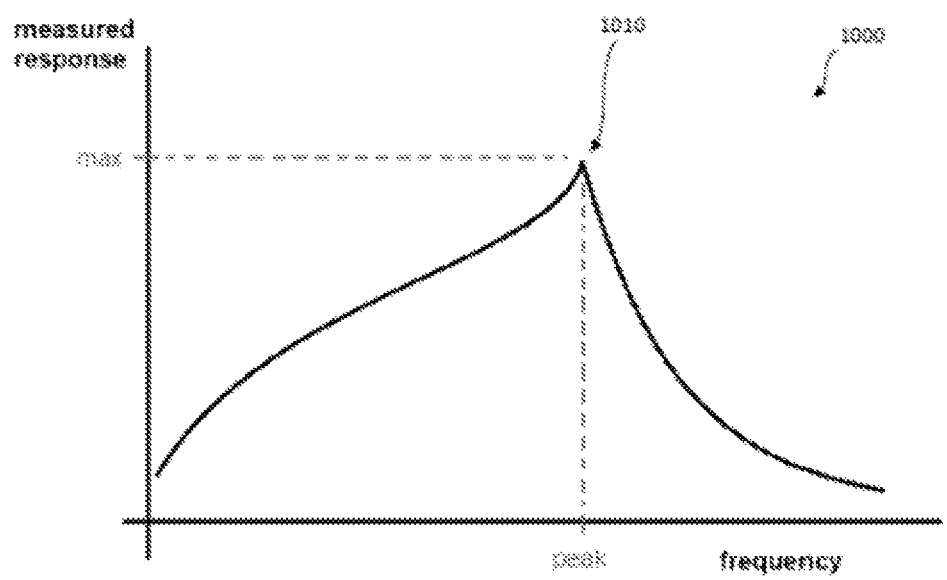
FIG. 10 is a graph illustrating an example of a plot, in accordance with an embodiment.

In an alternative embodiment, the viscoelastoplastic responses of the tissue is measured by using an impulse response. While the above scanned techniques seek to apply all frequencies, or a band of relatively wide frequencies, to the tissue to determine rheological parameters, there is another method to apply wideband frequencies, the impulse response. A delta forcing function can be Fourier-analyzed to demonstrate the delta function is composed of wideband frequencies appearing simultaneously in time, versus scanned, or spread out, in time. Like the striking a gong with a quick tap of a hammer: the tissue will respond with a primary peak response tone, as illustrated in FIG. 10, but also with overtones, harmonics and subharmonics with constitute portions of the frequency response. These responses provide the objective input to derive the rheological parameters of the system. The impulse, or tap, to the system may be provided as a single relatively rapid expansion of the shell 185 surrounding the treatment band 170, like a puff of air in a glaucoma test. The reaction of the tissue could be ascertained with sufficiently rapidly responding force sensors 171.

In accordance with one embodiment, upon insertion of the device 100 into the vagina, sensors 171 immediately sense certain parameters of the tissue, for example, the plastic deformation component of the tissue. Along with the sensors 171 measuring the reaction of the contracted muscles to the vibration of the device 100, sensors 171 may also detect the consistency of the tissue contraction around the device 100. By way of example, the sensors may measure whether the tissue strength remains the same throughout the predetermined duration, or whether the amount of force applied to the device weakens over the predetermined duration, i.e. determining a flicker score. As a further example, the sensors may measure the consistency of repeated contractions around the device 100.

The receiver/transmitter component 310 is configured to receive a communication from the external device 500 which may be stored in a device memory 330, as discussed with FIG. 4. The communication from the external device 500 may include instructions for the device 100 to change vibration frequency, vibration patterns, vibration duration, light intensity and/or light duration according to input from the external device 500.

Figure 5:
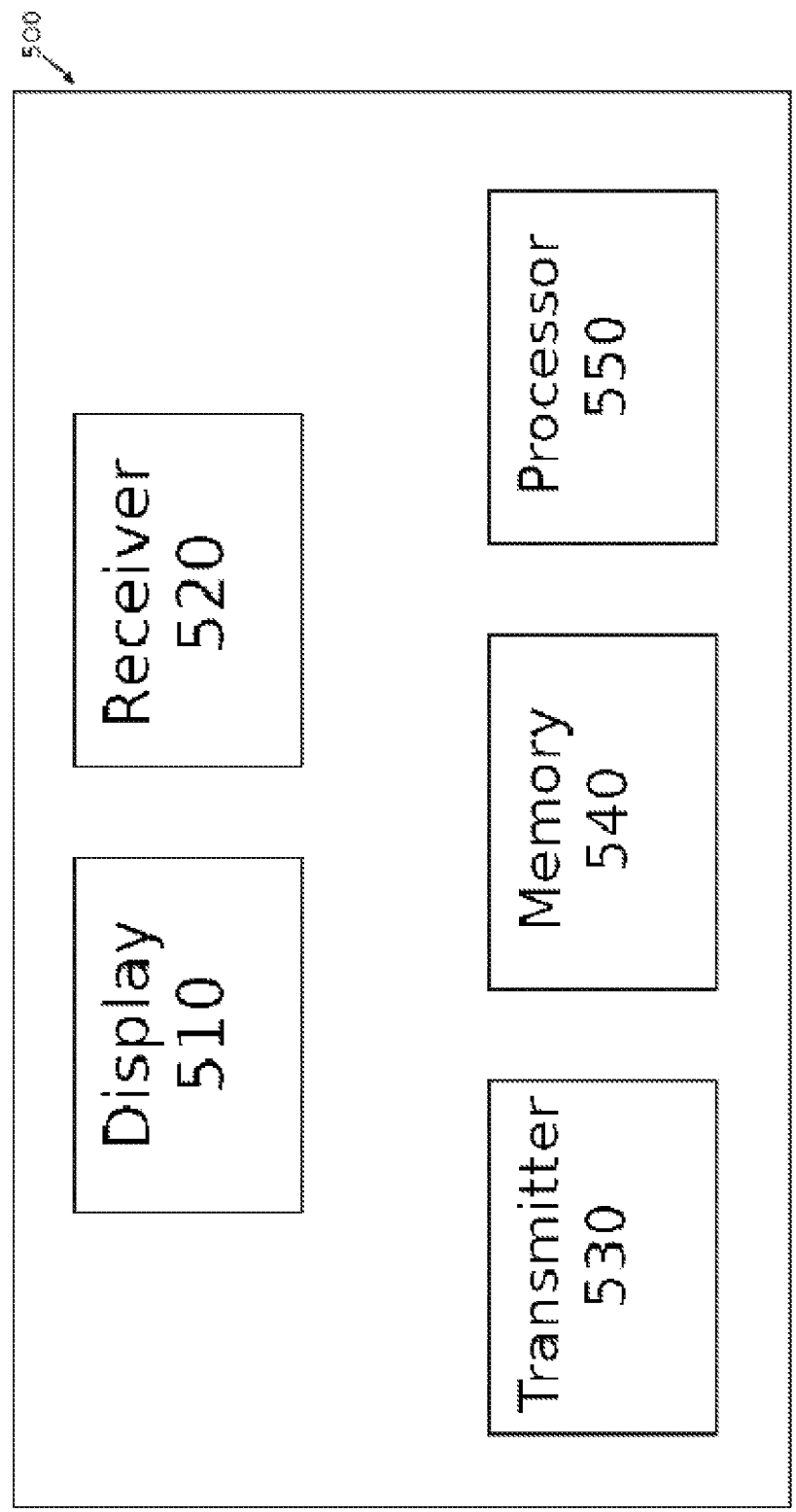
FIG. 5 is a block diagram of an external device, in accordance with an embodiment.

FIG. 5 is a block diagram of an embodiment of an external device 500 that communicates with device 100. The external device 500 includes display 510, a receiver 520, a transmitter 530, a memory 540 and a processor 550.

In accordance with one embodiment, processor 550 displays one or more windows on display 510 that solicit subjective information from the user. The subjective information may include, but is not limited to, the user still suffering incontinence issues, pain during sex, and/or that at least one of the symptoms seem to be improving. The subjective data may be solicited by asking a user a series of questions regarding how the user feels after a treatment session or a series of treatment sessions. These responses, in an embodiment, are transmitted using a transmitter 530 from the external device 500 to a cloud server. The cloud server may be accessed from the external device 500 from an app downloaded onto the external device 500 as discussed below in FIG. 11.

Figure 6:
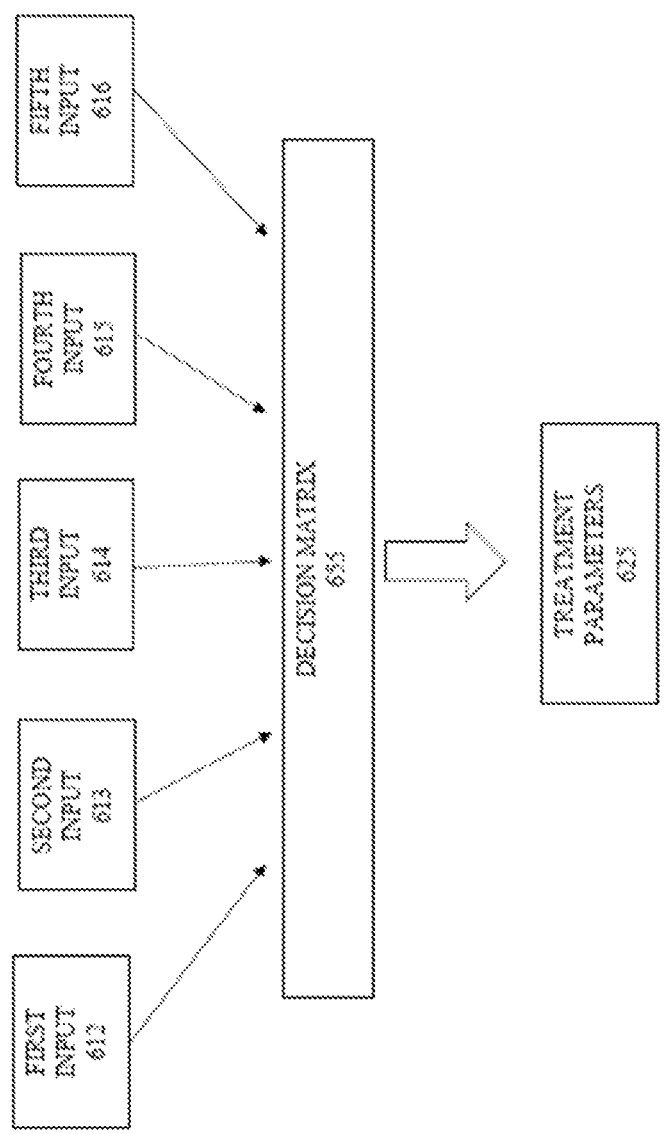
FIG. 6 is a block diagram of software components, in accordance with an embodiment.

FIG. 6 provides a block diagram of software components executed either by processor 320 of device 100 or processor 550 of external device 500 to determine treatment parameters based on subjective data received by processor 550 and objective parameters determined from the sensor data from sensors 171.

The software components include a first input 612, a second input 613, a third input 614, a fourth input 615 and a fifth input 616. First input 612 includes the subjective information solicited from the user. Second input 513 includes subjective and/or objective data provided by a medical professional, e.g. a doctor or a physical therapist and includes subjective and/or objective data based on an examination and/or interview of the user. The second input 513, in an embodiment is transmitted to the receiver 520 of the external device 500 or alternatively, directly to a cloud system or app. Third input 614 includes the objective parameters determined from the sensed values produced by the sensors 171 such as the viscosity, elasticity and plasticity values discussed above. The third input 614, in an embodiment is received by the receiver 520 of the external device 500 and in turn transmitted by the transceiver 530 of the external device 500 to the cloud or app. Fourth input 615 is an amount of charge remaining in power source 186. When external device 500 is used to determine the treatment parameters, external device 500 receives the amount of charge remaining in power source 186 from device 100 along with the sensor values or tissue parameters. Fifth input 616 includes a baseline of the objective parameters of third input 614 and indicates the values of the objective parameters before treatment began.

Figure 7:
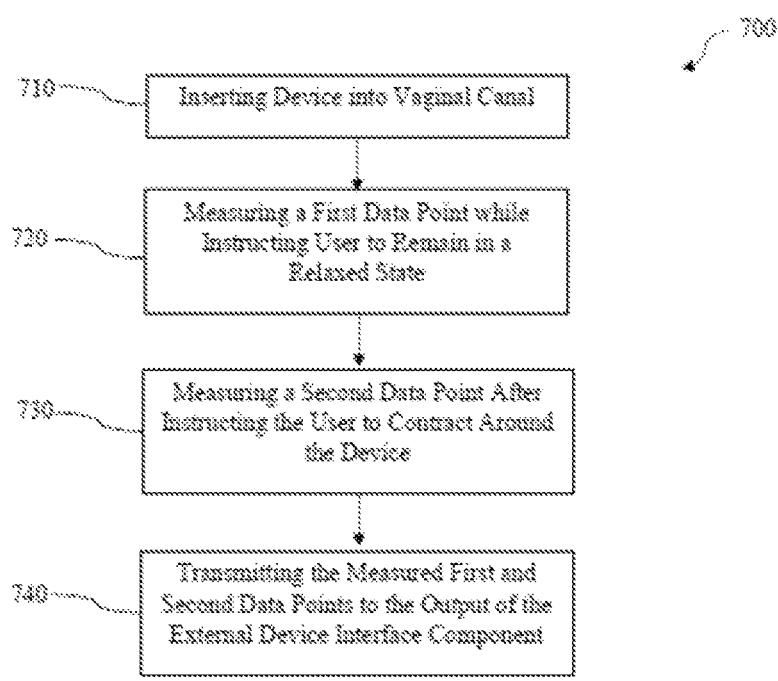
FIG. 7 is a flowchart of a method for determining baseline, in accordance with an embodiment.

FIG. 7 is a method 700 for establishing the baseline objective parameters of fifth input 616. First 710, inserting the device into the vaginal canal. Second 720, measuring a first data point(s) while instructing the user to remain in a relaxed state. The measurement(s) may be performed with or without vibration of the device. Third 730, measuring second data point(s) after instructing the user to contract the muscles around the device. This measurement may be performed with or without vibration and measures the amount of force or pressure applied to the sensors 171. Fourth, 740, using the measured data points to determine parameters of the tissue and storing the parameters as baseline values. In accordance with one embodiment, step 740 involves transmitting the measured first and second data points to external device 500, where processor 550 determines the tissue parameters from the data points and stores the tissue parameters in memory 540. Each of the subsequent measurements may be compared to this data. Further, using the baseline, a projected improvement may be calculated. By way of example, a user's tone baseline, or first data point, may be a certain number. Based on the user's age, number of children, or other factors, the user's tone may be calculated to improve by a range of 50-60%. This range becomes a target range for the user.

The software components of FIG. 6 also include a decision matrix 655 that applies the information from one or more of the inputs 612, 613, 614, 615 and 616 to determine parameters for treatment 625 including the length of light treatment, the length of vibration treatment, the intensity of light, the magnitude of vibration and the type of vibration. Each of the inputs are given a predetermined weight in the decision matrix. The objective data, input into the decision matrix 655 without additional data or input, will provide a calculated number for various factors such as a vibration level for the device 100, how long a user should contract around the device 100 and the duration for how long the device should be used. Although the objective device will provide a calculated value as to how much a user has improved, the objective data by itself does not include how the user is feeling after or during treatment. A user may objectively be improving, but subjectively there may be more or less improvement than what is objectively calculated. Thus, by allowing the user to input subjective data, the output from decision matrix 655 may be adjusted according to the combined objective and subjective data. For example, if the objective data indicates improvement in the tissue but the subjective data indicates that the user is still suffering from undesirable symptoms, the treatment plan may include an increased duration intensity for vibration treatment. Similarly, if the objective data indicates that the tissue is not improving but the subjective data indicates that the symptoms have improved, the length or intensity of treatment may also be increased. If the objective data or the subjective data indicates that the treatment should be increased but the charge of the power source indicates that the charge is insufficient to increase the length or intensity of both the light treatment and the vibration treatment, the treatment plan will choose the combination of light treatment and vibration that can be executed given the remaining charge of the power source that will maximize the treatment benefit to the user.

The decision matrix may alternatively be arranged in one or more servers, cloud or app, and the treatment plan determined by the decision matrix 655 is received by the receiver 520 by the external device 500 from the cloud or app via a Bluetooth connection with the servers. The external device 500 acts as an intermediary device to the treatment device 100. The treatment plan is thus managed, changed and adjusted through the servers. This configuration allows a third party, such as a medical professional, to adjust the treatment plan without needing to access the external device 500.

In a further embodiment, the decision matrix 655 is configured to automatically assess and analyze the inputs to determine a new treatment plan. Alternatively, the decision matrix 655 is configured to analyze the inputs when instructed to do so by the user or the third party.

In an embodiment, the treatment plan, or part of the treatment plan, that is output by the decision matrix 655 includes a scan across a range of frequencies, or a selected one or more predetermined optimal frequencies, and passively determines a tissue response to construct a model of the tissue state, i.e. 1-10 scale, better v. worse scales, detailed objective coefficient data. Similarly, the same technique may be used for light and/or thermal treatment.

In another embodiment, the treatment plan, or a part of the treatment plan, that is output by the decision matrix 655 uses a single, or a small range, of frequencies where some optimal response is occurring from the tissue. The treatment plan localizes the treatment to that frequency or amplitude of the frequency. Similarly, the same technique may be used for light and/or thermal treatment.

The new treatment plan may either be output onto display 510 of external device 500 or may be output directly to the device processor 320 of treatment device 100 through the external device transmitter 630 to act as the user selected settings for the next treatment. The output, or treatment 625, from the decision matrix 655 may consist of a vibration setting, a duration setting and/or provide a user with instructions for the length of time to contract around the device 100 and at what intervals i.e. contract for 30 seconds and rest for 20 seconds.

In a further embodiment, processor 550 displays a history of determined tissue parameters on display 510 to provide the user a visual comparison of the user's present status versus their past status. For example, processor 550 plots a graph of the tissue parameters as a function of time. In some embodiments, processor 550 may also display a projected status expected after completing one or more additional treatments. The projected status is based on various factors such as age and/or number of children, thus the projection may be adjusted according to individual factors. This adjustment may be performed within the external device 500 using the decision matrix 655 or the adjustment may be manually performed by a medical professional or the user.

Figure 8:
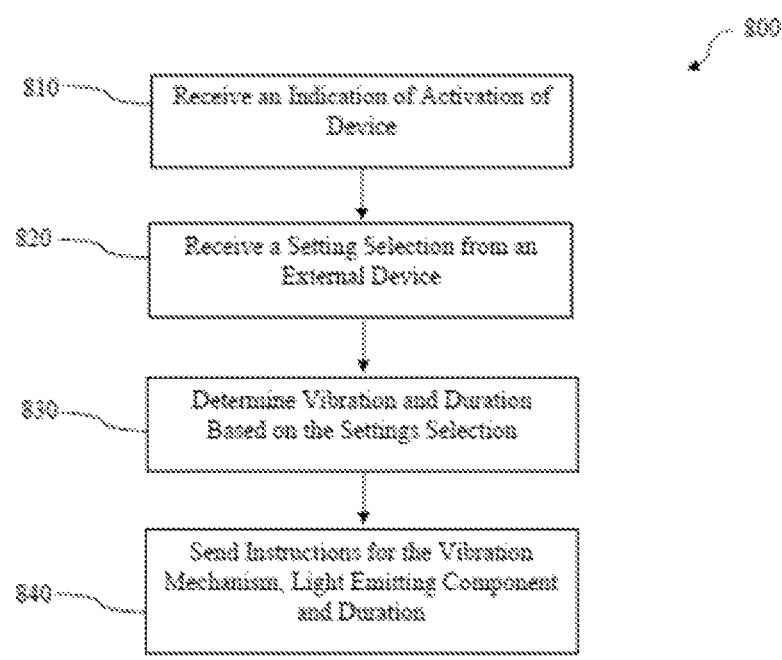
FIG. 8 is a flowchart of a method for inducing neocollagenesis, neoelastogenesis and neofibrogenesis, in accordance with an embodiment.

FIG. 8 is a flowchart of one embodiment of a method 800 for vaginal rejuvenation. In one embodiment, the method 800 is a sequential process starting with remodeling of the ECM including collagen and elastin and ending with effecting fibrotic responses to assist in remodeling of the ECM, consequently tightening the vaginal tissue and vaginal lumen. In another embodiment, the method 800 remodels the ECM while simultaneously effecting fibrotic responses to assist in remodeling the ECM and consequently tightening the vaginal tissue and vaginal lumen.

An indication is received 810 by processor 320 that a user has activated the treatment device. The indication may include notification that the device has been placed into contact with vaginal tissue from a sensor used to detect contact between the device and vaginal tissue. Contact of vaginal tissue with the device or presence of vaginal tissue within a threshold distance with the device can also be detected using optical sensors, capacitive sensors (detecting capacitive proximity), as well as any other suitable proximity sensor. The indication could also be a notification that the user has turned on the device or activated a particular setting.

Setting selections are received 820 or retrieved from memory (e.g., the settings are received from the user or from the external device 500 or are retrieved from memory 330) to control the vibrating device and lights of the device. For example, the user may select a vibration speed or pattern. In one embodiment, no setting selections are selected by the user and, in another embodiment, one or more setting selections are selected. In a further embodiment, the external device 500 determines the selections based on the discussed subjective and objective input. Based on the setting selections, light intensity, vibration, vibration intensity and duration are determined 830. The device will vibrate at the selected vibration setting. If a duration has been set, the device will operate for the duration setting. Similarly, if the instructions regarding the setting were received 820 or retrieved from within the device in an automatic setting selection mode, the device will institute the setting. In other embodiments, if not all setting selections are selected by the user, a default setting for each setting with no setting selection will be determined. Instructions including the determined settings for vibration, vibration intensity and duration are then used by device 100 at step 840.

Figure 9:
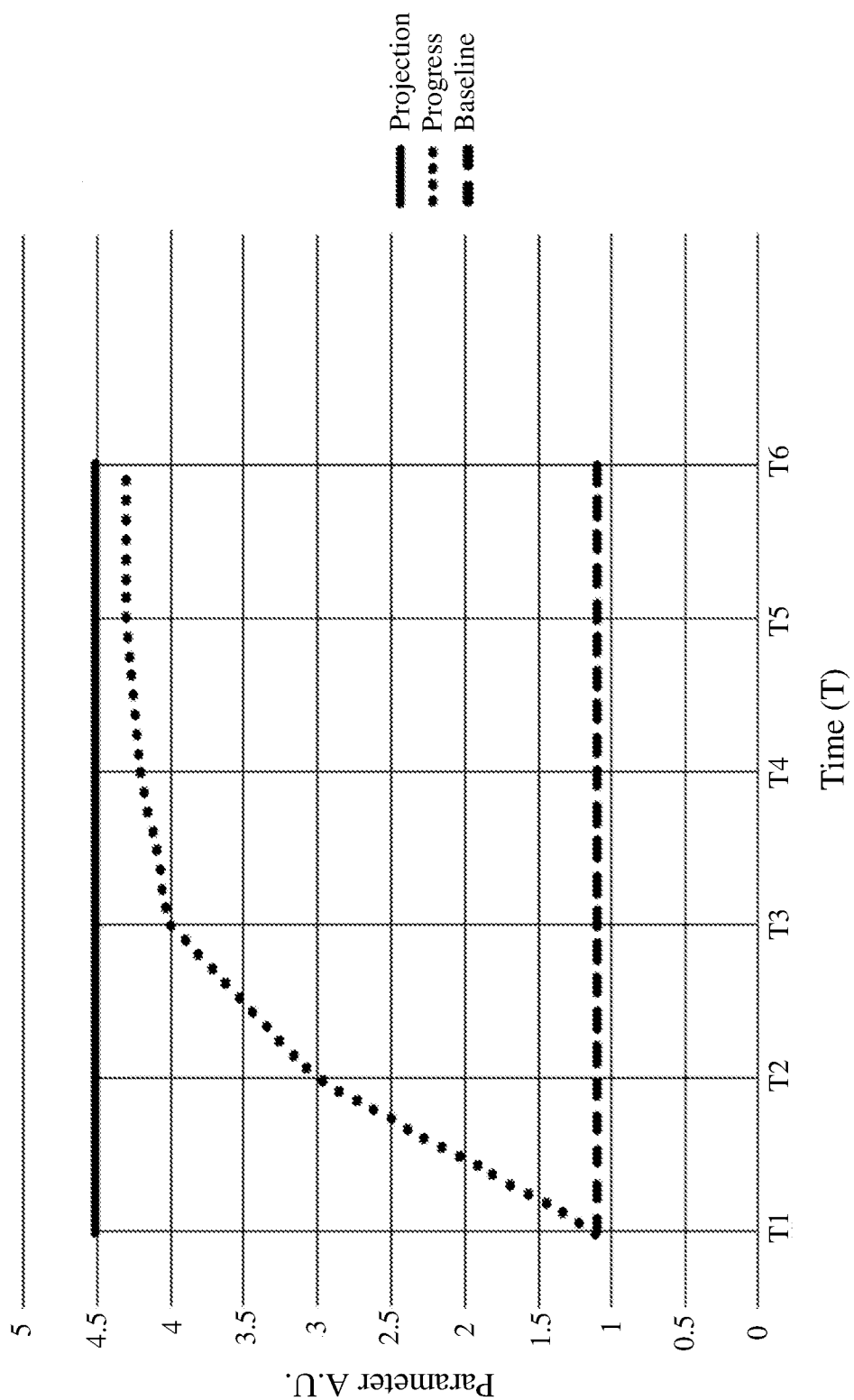
FIG. 9 is a graph illustrating an example of a plot, in accordance with an embodiment.

FIG. 9 illustrates an example of a plot 900 as discussed in conjunction with the processor 550 of the external device 500 in FIG. 5. A baseline 910, indicated with the dashed line, may be a baseline for any of the above discussed tissue parameters. This indicates to the user where they started in the treatment and offers a comparison of where the user started versus where they are after beginning treatment. Thus, progress may be seen by the user. A projection 920, indicated by the solid line, indicates to the user a target tissue parameter of the treatment plan. This indicates a goal to reach and shows how far the user is from reaching the projection 920. This projection 920 may be set by the user, a medical professional working with the user in a treatment plan, or may be set by the device 100 or external device 500 using an algorithm taking into account user statistics, i.e. age, number of children, etc. In an embodiment, progress 930, indicated by the dotted line, is tracked over time (T). In an embodiment, time is a measurement of each use of the device 100 by the user, i.e. use 1, use 2, use N, where the time between each use is arbitrary. In an alternative embodiment, time may be measured as the progress over a certain time period such as a course of weeks or months. The user can use the plot of the parameters for a visual assessment of their progress 930 from where they started, the baseline 910, to where they need to be in their treatment plan, the projection 920.

FIG. 10 illustrates a further example of a plot 1000 as discussed in conjunction with the processor 550 of the external device 500 in FIG. 5. The plot 1000 illustrates a tissue response curve to a forcing function scanned across a range of frequencies. As illustrated the peak location 1010, both in amplitude and in frequency space, has objective meaning in terms of characteristic viscoelastoplastic tissue parameters. As discussed above, a baseline of the tissue response curve may be plotted against a target tissue response curve. The progress of the user is then measured against the baseline and the projected curves.

FIG. 11 illustrates an embodiment of an app 1100 for using the device 100 according to a treatment plan. The app is downloaded onto the external device 500 and linked to the above-mentioned cloud server. The app 1100 may include gamification 1110, a controller 1115 portion in connection with the device 100 allowing the controller 1115 to operate portions of the device 100, i.e. the light-emitting component 171, the vibrating component 172 and the other components included on the device 100. Further, the app 1000 may include a treatment calendar 1120 to provide the user with a view of when the device should be used according to the treatment plan and/or when the device 100 has been used according to the treatment plan. An additional aspect of the app is a progression 1125 portion where a user views their progress in the treatment plan, as discussed with FIGS. 9 and 10. The app 1000 is accessible by the user and/or a third party, i.e. a medical professional.

In an example of the gamification 1110 aspect of the app 1000, the user is instructed to follow a pattern while undergoing treatment, i.e. contract tissue around the device 100 for 2 seconds, release for 4 seconds and repeating for a predetermined number of iterations. The user uses the external device 500 with the app 1000 to see the realization of their progress on the display 510. In another example, a user is instructed to contract the tissue about the device for a certain amount of time or exert a certain amount of force on the device 100 which is monitored by the external device 500 which communicates the information to the app 1000 and illustrates the results of the exercise on the display 510. Should the user reach the goal, a digital badge of encouragement or achievement is issued. In a further example, digital badges are issued by the app or external device 500 for staying on the treatment plan, i.e. a gold star once the user reaches two weeks of using the treatment plan and a platinum star when the user reaches three weeks of using the treatment plan.

Although this description discusses vaginal health, the discussed embodiments may also be applied to treatments for anal disorders such as fecal incontinence, where device is inserted into an anal cavity to measure anal health.

Although elements have been shown or described as separate embodiments above, portions of each embodiment may be combined with all or part of other embodiments described above.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms for implementing the claims.

What is claimed is:

1. A treatment system comprising:
    a treatment device including a semi-rigid shell forming an external surface, at least part of the external surface of the shell adapted to contact tissue of a body cavity, the shell comprising:
        a treatment band formed around a circumference of the shell,
        a first portion forming a rounded end of the device that is distal to the treatment band, and
        a second portion formed around the circumference of the shell and located proximal to the treatment band;
        a vibration mechanism coupled to one or more portions of an inner wall of the shell;
        a force sensor configured to provide objective data by measuring a reaction of the tissue that is in contact with the external surface of the shell while the vibration mechanism is activated or while the vibration mechanism is inactive;
    an external device configured to receive subjective information provided by a user or a third party and to receive the objective data from the treatment device, the external device including a processor configured to use the subjective information and the objective data in a decision matrix to issue commands to at least the vibration mechanism that correspond to treatment instructions based on the subjective information and the objective data, wherein the treatment instructions include instructions related to a treatment vibration frequency and a treatment duration.

2. The system of claim 1, wherein the treatment device further comprises a receiver configured to receive data from the external device and a transmitter configured to transmit data to the external device.

3. The system of claim 1, wherein the objective data is converted to parameters of the tissue, wherein the parameters of the tissue comprise viscous, elastic and plastic deformation characteristics of the tissue from the measured reaction of the tissue.

4. The system of claim 1, wherein the force sensor comprises a plurality of force-sensing elements arranged around the circumference of the shell.

5. The system of claim 3, wherein the treatment device comprises a memory that stores the parameters of the tissue to transmit to the external device.

6. The system of claim 1, wherein the treatment device comprises a processor configured to receive the treatment instructions from the external device.

7. The system of claim 6, wherein the treatment instructions further comprise at least one of:
    a treatment temperature, wherein the processor of the treatment device sets a heat mechanism of the treatment device to the treatment temperature during the treatment; and
    a treatment light intensity, wherein the processor of the treatment device sets a light emitting component of the treatment device to the treatment light intensity during the treatment; and
    wherein the treatment duration is an operational time limit for the vibration mechanism and for the light emitting component or the heat mechanism.

8. A method comprising:
    activating a force sensor that is within a treatment device while the treatment device is in contact with tissue of a body cavity of a user;
    collecting sensor data from the force sensor that is within the treatment device to measure a reaction of the tissue that is in contact with the treatment device;
    converting the sensor data into parameters of the tissue;
    applying the tissue parameters to a decision matrix; and
    applying subjective information from the user or a third party to the decision matrix;
    wherein the decision matrix determines treatment settings to be applied to the tissue by the treatment device including at least a treatment vibration frequency provided by a vibrating component and a treatment duration.

9. The method of claim 8, further comprising:
    instructing a user to contract muscles of the body cavity around the treatment device;
    collecting sensor data from the force sensor while the vibrating component is activated and while the user contracts muscles around the treatment device to measure the reaction of the tissue that is in contact with the treatment device;
    converting the sensor data into a further tissue parameter; and
    applying the further tissue parameter to the decision matrix.

10. The method of claim 8, further comprising storing the treatment settings in a memory of the treatment device such that the treatment settings are automatically used by the treatment device during a next treatment.

11. The method of claim 8, further comprising instructing a user to relax muscles of the body cavity around the treatment device when collecting the sensor data.

12. The method of claim 8, further comprising applying current battery charge of the treatment device to the decision matrix to determine treatment settings, wherein at least the treatment duration is based in part upon the current battery charge.

13. The method of claim 8, wherein the subjective information is indicative of improvement in a user's symptoms.

14. An external device configured to communicate with a treatment device, the external device comprising:
  an interface configured to receive subjective information, wherein subjective information is provided by a user or a third party;
  a receiver configured to receive objective data from the treatment device, wherein the objective data include tissue parameters determined from sensor data generated by a force sensor of the treatment device while a vibrating component located within the treatment device is active or while the vibrating component is inactive;
  a processor implementing a decision matrix configured to use at least the subjective information and the objective data to select treatment settings for the treatment device, the treatment settings including at least a treatment vibration frequency and a treatment duration; and
  a transmitter configured to communicate the treatment settings to the treatment device.

15. The device of claim 14, wherein the tissue parameters include at least one of a viscous response, an elastic response and a plastic response of the tissue.

16. The device of claim 14, wherein the subjective information is provided by a user using a series of interview questions corresponding to how the user feels health-wise after a treatment session or series of treatment sessions.

17. The device of claim 14, wherein the subjective information and the objective data are each given a respective weight in the decision matrix such that if one of the subjective information and the objective data is indicative of tissue improvement and the other of the subjective information and the objective data is indicative of tissue no improvement then the treatment settings are selected to increase vibration intensity and duration.

18. The device of claim 14, wherein the processor generates a plot of the objective data on the user interface of the device.

19. The device of claim 14, wherein the external device communicates with at least one server.

20. The device of claim 14, wherein the decision matrix is further configured to use the battery charge of the treatment device to determine treatment settings, wherein at least the treatment duration is based in part upon the current battery charge.

* * * * *